US012390549B2

(12) United States Patent
Nasui

(10) Patent No.: US 12,390,549 B2
(45) Date of Patent: Aug. 19, 2025

(54) AIRBORNE VIRUS PROTECTION AND DISINFECTION DEVICE AND METHOD OF MANUFACTURING

(71) Applicant: American International Radio, Inc., Rolling Meadows, IL (US)

(72) Inventor: Dorel Vasile Nasui, Deer Park, IL (US)

(73) Assignee: American International Radio, Inc., Rolling Meadows, IL (US)

(*) Notice: Subject to any disclaimer, the term of this patent is extended or adjusted under 35 U.S.C. 154(b) by 358 days.

(21) Appl. No.: 17/304,753

(22) Filed: Jun. 25, 2021

(65) Prior Publication Data

US 2022/0257822 A1 Aug. 18, 2022

Related U.S. Application Data

(60) Provisional application No. 63/200,149, filed on Feb. 17, 2021.

(51) Int. Cl.

| | |
|---|---|
| ***A61L 9/22*** | (2006.01) |
| ***A61L 9/14*** | (2006.01) |
| ***A61L 9/20*** | (2006.01) |

(52) U.S. Cl.

CPC ..... *A61L 9/22* (2013.01); *A61L 9/14* (2013.01); *A61L 9/20* (2013.01); *A61L 2209/213* (2013.01)

(58) Field of Classification Search

CPC ..... A61L 9/22; A61L 9/14; A61L 9/20; A61L 2209/213; A61L 9/18; A61L 2209/15; A61L 2202/25; A61L 2209/14; A61L 2/10; A61L 2202/122; A61L 2101/26; A61L 2209/134; A61L 2202/11; A61L 2202/26; A61L 2209/12; B03C 3/383; B03C 3/60; B03C 3/32; B03C 3/368; B03C 3/016; B03C 2201/10; A61M 16/1065;

(Continued)

(56) References Cited

U.S. PATENT DOCUMENTS 10,905,790 B1 * 2/2021 Moore ..................... A61L 2/10
2004/0216745 A1 * 11/2004 Yuen ..................... A62B 19/00
128/205.27

(Continued)

FOREIGN PATENT DOCUMENTS

WO 2005060366 A2 7/2005

*Primary Examiner* — Xiuyu Tai

(74) *Attorney, Agent, or Firm* — Ziolkowski Patent Solutions Group, SC

(57) ABSTRACT

An airborne virus protection and disinfection (AIRVPD) device includes positive and negative electrodes arranged to form an electrode fluid path therebetween and a high-voltage converter configured to deliver power to the positive and negative electrodes to trigger a redox reaction. The AIRVPD device also includes a chemical disinfecting unit having a sponge material associated with at least one of the positive and negative electrodes and capable of becoming impregnated with an antimicrobial capable of killing airborne viruses. The AIRVPD device further includes a housing encasing the positive and negative electrodes, the high-voltage converter, and the chemical disinfecting unit. The housing includes an inlet and an outlet in fluid communication with each other via the electrode fluid path. Ionized air with charged droplets external to the AIRVPD device is able to flow through the AIRVPD device for disinfection and neutralization.

20 Claims, 10 Drawing Sheets

(58) Field of Classification Search
CPC ...... A61M 16/06; A62B 23/025; A62B 23/02; A62B 7/10
See application file for complete search history.

(56) References Cited

U.S. PATENT DOCUMENTS

| | | | | |
|---|---|---|---|---|
| 2010/0307332 | A1* | 12/2010 | Yuen | B03C 3/383<br>96/25 |
| 2012/0274933 | A1* | 11/2012 | Doucette | B03C 3/016<br>356/301 |
| 2019/0175779 | A1* | 6/2019 | Baek | A61L 9/22 |
| 2020/0009577 | A1 | 1/2020 | Hepperle et al. | |

* cited by examiner

AIRBORNE VIRUS PROTECTION AND DISINFECTION DEVICE AND METHOD OF MANUFACTURING

CROSS-REFERENCE TO RELATED APPLICATION

The present invention claims the benefit of U.S. Provisional Patent Application Ser. No. 63/200,149, filed Feb. 17, 2021, the disclosure of which is incorporated herein by reference in its entirety.

BACKGROUND OF THE INVENTION

Embodiments of the present invention relate to a device for protecting against airborne viruses, and, more particularly, to a device that collects and disinfects droplets of infected bodily fluid in air to prevent the spread of airborne viruses.

Airborne viruses are those that are capable of becoming suspended in air. Many airborne viruses plague humans, animals, or both throughout the world. Some examples of airborne viruses are rhinoviruses that cause common cold symptoms, influenza viruses, varicella viruses, the measles virus, the mumps virus, the hanta virus, viral meningitis, severe acute respiratory syndrome (SARS), and coronaviruses such as, for example, coronavirus disease 2019 (COVID-19). Airborne viruses tend to spread easily and quickly and, as such, are often harder to control than pathogens that spread in other ways.

Those who have not yet established an immunity to an airborne virus, either by way of already being infected or by vaccination, and those who have underlying illnesses or weakened immune systems that make them more likely to get an infection are susceptible to airborne viruses. Individuals infected with airborne viruses will typically spread them when they cough or sneeze, but can also spread them by merely breathing or talking. Regardless of how airborne viruses are expelled from a host, airborne viruses can infect individuals in different ways. Some airborne viruses can live on surfaces for a period of time and be transmitted when people touch the surface and then their eyes, noses, or mouths. Further, airborne viruses are so small that they essentially become an aerosol that may infect a number of individuals who breathe in the infectious aerosol.

Most airborne viruses are fairly unstable after leaving the bodies of their hosts, but droplets of infected bodily fluids, and especially micro droplets, exhaled by infectious people can remain suspended for hours and travel far distances on air currents. Thus, although transmission by way of these respiratory droplets is most likely to occur in close proximity to infectious people—generally within six feet—people can still be exposed to the droplets at greater distances from infectious people and many hours after they have left the area, as long as the droplets are allowed to remain in the air and/or on surfaces. People utilize many types of equipment and materials in attempting to prevent the spread of airborne viruses by droplets. For example, people will often wear and/or use face masks and shields, glasses, gloves, disinfecting wipes, hand sanitizer, and antibacterial hand soap. However, none of these can guarantee total protection from and/or disinfection of airborne viruses, even when they are used together.

It would therefore be desirable to provide a device that can protect against airborne viruses while also disinfecting airborne viruses.

BRIEF STATEMENT OF THE INVENTION

Embodiments of the present invention are directed to an airborne virus protection and disinfection (AIRVPD) device that prevents contact with airborne viruses and disinfects airborne viruses simultaneously.

In accordance with one aspect of the invention, an AIRVPD device includes a positive electrode and a negative electrode in close proximity to, but spaced away from, the positive electrode to form an electrode fluid path between the positive and negative electrodes. The AIRVPD device additionally includes a high-voltage converter configured to deliver power to the positive and negative electrodes in order to trigger a redox reaction at each of the positive and negative electrodes such that the positive electrode attracts negatively charged particles and the negative electrode attracts positively charged particles. Furthermore, the AIRVPD device includes a chemical disinfecting unit having a sponge material associated with and extending along a length of at least one of the positive and negative electrodes. The sponge material is capable of becoming impregnated with an antimicrobial capable of killing airborne viruses. Moreover, the AIRVPD device includes a housing encasing the positive and negative electrodes, the high-voltage converter, and the chemical disinfecting unit and including an inlet and an outlet in fluid communication with each other via the electrode fluid path. The housing is configured such that ionized air with charged droplets external to the AIRVPD device is able to flow into the AIRVPD device through the inlet of the housing, through the electrode fluid path for disinfection by the antimicrobial and for neutralization by the positive and negative electrodes, and through the outlet of the housing and out of the AIRVPD device.

In accordance with another aspect of the invention, a kit for protection against and disinfection of airborne viruses includes an ionizer configured to produce ions for electrically charging air having droplets and at least one AIRVPD device. The at least one AIRVPD device includes a converter configured to convert a power from a power supply to a high-voltage, low-current power across a positive side and a negative side thereof and a pair of electrodes having a cathode coupled to the negative side of the converter and an anode coupled to the positive side of the converter and positioned adjacent to, but electrically isolated from, the cathode. The cathode and anode are configured to receive the high-voltage, low-current power from the converter to induce a redox reaction at the cathode and anode and are arranged to form an electrode fluid path therebetween. The at least one AIRVPD device also includes a chemical disinfecting unit with a sponge material arranged on at least one of the cathode and anode and capable of impregnation with an antimicrobial capable of killing airborne viruses. The sponge material is configured to supply the antimicrobial to the at least one of the cathode and anode. In addition, the at least one AIRVPD device includes a case positioned around the converter, the pair of electrodes, and the chemical disinfecting unit. The case includes an inlet and an outlet in fluid communication with each other through the electrode fluid path. Ionized air having charged droplets is able to flow into the AIRVPD device through the inlet of the case, along the electrode fluid path for charge neutralization and disinfection, and through the outlet of the case to exit the AIRVPD device.

In accordance with yet another aspect of the invention, a method of manufacturing an AIRVPD device includes arranging a pair of electrodes comprising a positive electrode and a negative electrode in close proximity to, but electrically isolated from, one another to form an electrode fluid path therebetween. The method further includes coupling a high-voltage converter to the positive and negative electrodes for introducing a redox reaction at the positive and negative electrodes and positioning a chemical disinfecting unit including a sponge material capable of becoming impregnated with an antimicrobial adjacent to at least one of the positive and negative electrodes to deliver the antimicrobial to the at least one of the positive and negative electrodes adjacent thereto. The method additionally includes encasing the positive and negative electrodes, the high-voltage converter, and the chemical disinfecting unit in a housing comprising an inlet and an outlet in fluid communication with each other and the electrode fluid path.

Various other features and advantages of the present invention will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

Embodiments of the present invention provide for an AIRVPD device and a method for making the same. The AIRVPD device has positive and negative electrodes in close proximity to, but spaced away from, each other such that they are electrically isolated from each other. The AIRVPD device also includes a converter configured to deliver a high-voltage, low-current power to the positive and negative electrodes in order to trigger a redox reaction at each of the positive and negative electrodes so that the positive and negative electrodes attract negative and positive particles, respectively. At least one of the positive and negative electrodes is associated with a chemical disinfecting unit that supplies an antimicrobial capable of killing airborne viruses to the positive electrode and/or negative electrode. A housing having an inlet and an outlet encases the positive and negative electrodes, converter, and chemical disinfecting unit. A flow path through the inlet, between the positive and negative electrodes, and through the outlet allows ionized air having charged droplets of bodily fluid to flow through the AIRVPD device for charge neutralization and disinfection of airborne viruses.

Figure 1:
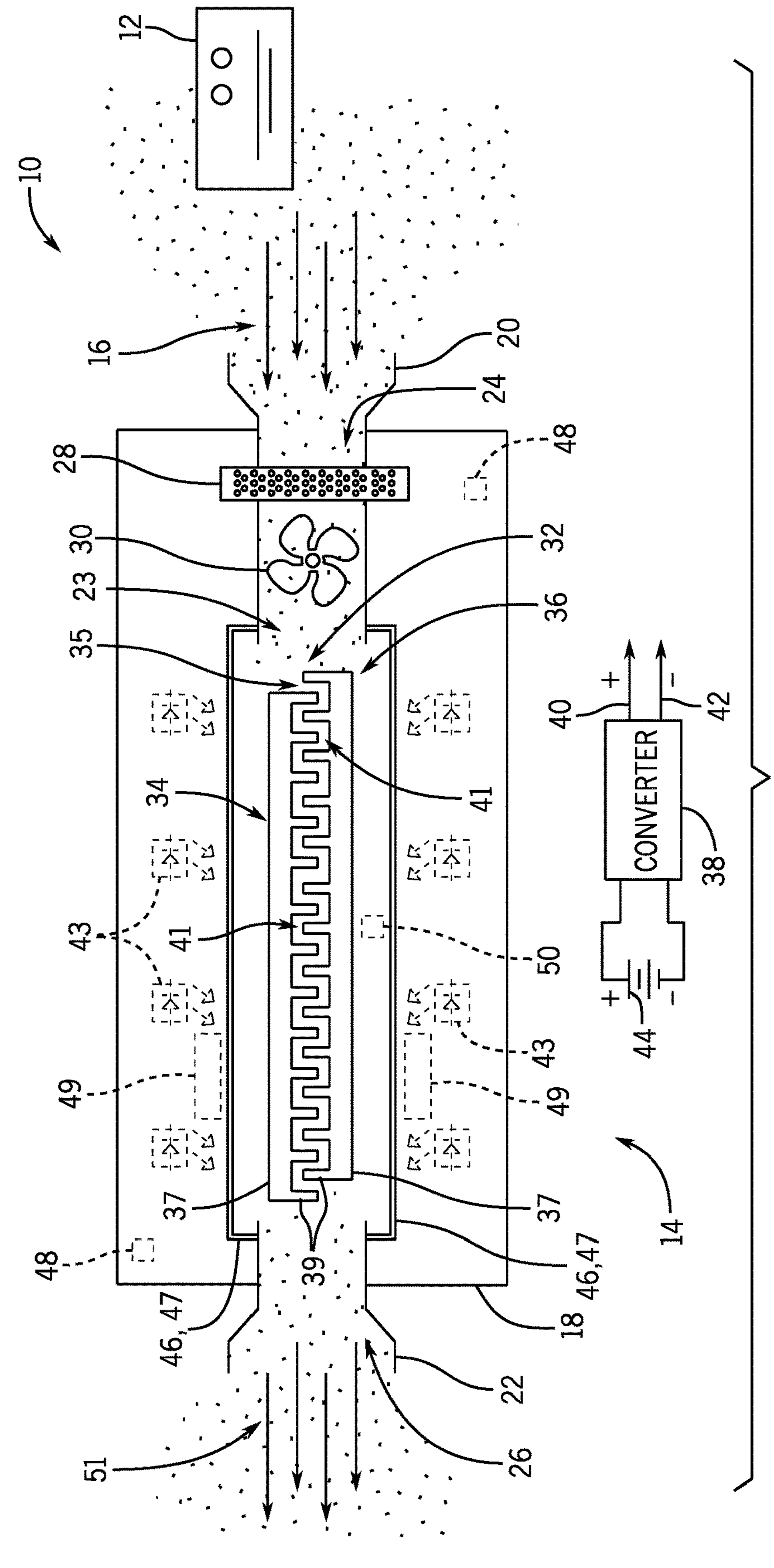
FIG. 1 is a block diagram of an AIRVPD system including an AIRVPD device, according to an embodiment of the invention.

Referring to FIG. 1, a block diagram of a system 10 for protection against and disinfection of airborne viruses having an ionizer 12 and an AIRVPD device 14 is shown, according to an embodiment of the invention. Ionizer 12 uses a high voltage to provide either a positive or negative electrical charge to air particles that move through ionizer 12. As a result ionizer 12 produces a plurality of air ions that are introduced into the environment. These air ions are intercepted by droplets of bodily fluid shed from individuals due to breathing, talking, coughing, sneezing, and any other actions that result in droplets of bodily fluid being expelled into the environment. These droplets may include both non-infected droplets and droplets infected with airborne viruses. In either case, the droplets obtain a strong electrical charge when they intercept the air ions. As a non-limiting example, the charge of the droplets may increase by approximately 10 times after interception of the air ions. The type of charge will depend on the charge of the air ion(s) intercepted by the droplets. Regardless, the operation of ionizer 12 results in ionized air with charged droplets 16 that may be drawn into AIRVPD device 14 for disinfection.

AIRVPD device 14 is positioned in the area of ionizer 12 such as, for example, adjacent ionizer 12 or at least in the same room as ionizer 12. Alternatively, ionizer 12 may be coupled to inlet 20 or be built into AIRVPD 14. As will discussed in more detail below with respect to FIGS. 2-12, AIRVPD device 14 may be constructed as a device for either personal use, use with an apparatus, use in an entire room, or use in a larger area. AIRVPD device 14 includes a housing or case 18 having an inlet 20 and an outlet 22 in fluid communication with each other through an interior 23 thereof. Each of inlet 20 and outlet 22 includes at least one respective opening 24, 26, but may include a plurality of openings 24, 26. Housing 18 may be made from conductive materials (for example, metallic materials such as aluminum), non-conductive or electrically insulating materials (for example, plastic), or a combination of such materials. However, non-conductive materials are preferred to aid in keeping components of AIRVPD device 14 electrically isolated from each other.

A high-efficiency particulate air (HEPA) filter 28 is positioned just inside interior 23 of housing 18 through inlet 20 for filtering ionized air with droplets 16 flowing into AIRVPD device 14. A fan 30 is positioned behind HEPA filter 28 such that ionized air with charged droplets 16 must flow through HEPA filter 28 before reaching fan 30. When AIRVPD device 14 is a personal or smaller modular device, fan 30 does not need to be especially powerful and may be a small, quiet device that is not burdensome to a user of AIRVPD device 14 by either its size or noise generated. When AIRVPD device 14 is a larger modular device or configured for a specific apparatus or area, fan 30 may be larger and more powerful. In fact, fan 30 may optionally be positioned external to housing 18 in some embodiments.

In various embodiments, fan 30 may have an airflow range of approximately 35 cubic feet per minute (approximately 0.016 cubic meters per second) to approximately 3,000 cubic feet per minute (approximately 1.42 cubic meters per second), depending on the size of the room in which AIRVPD device 14 is located and how many AIRVPD devices 14 are being utilized in the room. As a non-limiting example of fan 30, when fan 30 is used a single room with a volume of approximately 1,400 cubic foot (approximately 40 cubic meter), fan 30 may have an airflow of at least approximately 35 cubic feet per minute (approximately 0.016 cubic meters per second). Regardless of the configuration of fan 30, fan 30 is designed to create a jet or blade of fluid around housing 18 in order to attract ionized air with droplets 16 into housing 18. This jet or blade of fluid collects the ionized air with charged droplets 16 before any infected droplets of bodily fluid can reach an individual.

AIRVPD device 14 also includes a pair of electrodes 32 including a positive electrode or anode 34 and a negative electrode or cathode 36 within interior 23 of housing 18. Cathode 34 and anode 36 are made from a conductive material such as, for example, aluminum, copper, silver-plated copper, sponge copper, or silver-plated sponge copper. In a non-limiting example, anode 34 is made of copper, and cathode 36 is made of silver-plated sponge copper. In general, a length of anode 34 and cathode 36 extends through as much of interior 23 of housing 18 as possible. Anode 34 and cathode 36 are positioned in close proximity with one another. However, anode 34 and cathode 36 are spaced away from each other such that they are electrically isolated from each other by air. Additionally, even when housing 18 is formed of non-conductive materials, anode 34 and cathode 36 are typically electrically isolated from housing 18 by a high-voltage isolation or insulation material (not shown for simplicity), such as, for example, polytetrafluoroethylene (PTFE), ceramic, porcelain, silicone, or epoxy, to avoid creating a path directly between anode 34 and cathode 36 due to issues such as, for example, the aging of materials, moisture absorption, and impurities. As a non-limiting example of the distance between anode 34 and cathode 36, anode 34 and cathode 36 may be spaced apart at any point by a distance in a range between approximately 0.1 inches (0.254 centimeters) and approximately 0.2 inches (0.508 centimeters). Since anode 34 and cathode 36 are spaced apart from each other, an electrode fluid path 35 is present between anode 34 and cathode 36 where air can flow from inlet 20 of housing 18 to outlet 22 of housing 18.

Anode 34 and cathode 36 may be constructed in a variety of shapes. As non-limiting examples, anode 34 and cathode 36 may be constructed as straight cylindrical or square sections. However, since straight cylindrical and square section designs will not maximize the area of anode 34 and cathode 36 exposed to air, other designs may result in a greater efficiency. As a non-limiting example, anode 34 and cathode 36 may be constructed in a hair comb style arrangement such as that shown in FIG. 1. That is, each of anode 34 and cathode 36 includes a respective base 37 and a plurality of fins 39 extending substantially perpendicular to base 37. Adjacent fins 39 are spaced apart from each other by cavities 41. By arranging anode 34 and cathode 36 in an alternating manner such that fins 39 of anode 34 extend into cavities 41 of cathode 36 and fins 39 of cathode 36 extend into cavities 41 of anode 34, the design resembles a hair comb and results in an arrangement that will expose anode 34 and cathode 36 to more air than a straight cylindrical or square design. Thus, the hair comb style arrangement will operate more efficiently than a straight cylindrical or square design.

Further, at least one of anode 34 and cathode 36 is associated with a chemical disinfection unit 46. Chemical disinfection unit 46 is positioned adjacent to, coupled to, or integrated or built into anode 34 and/or cathode 36 and generally included in the form of a porous or sponge material 47, but may alternately or additionally include one or more reservoirs or storage tanks 49. As non-limiting examples, sponge material 47 may be made from sponge copper or silver-plated sponge copper and may be shaped as a strip or other convenient shape, depending on the shape of housing 18. Sponge material 47 is typically located along at least most of the length of and adjacent base 37 of its associated anode 34 and/or cathode 36 opposite fins 39. Reservoirs 49 are typically located adjacent sponge material 47 or adjacent base 37 of its associated anode 34 and/or cathode 36 opposite fins 39.

Sponge material 47 and reservoirs 49 will be impregnated with or contain an antimicrobial, such as, for example, an antiseptic, disinfectant, or germicide, that will kill airborne viruses on contact. The antimicrobial may include a high concentration of alcohol such as, for example, at least 50% alcohol. The purpose of chemical disinfecting unit 46 is to dispense the antimicrobial onto anode 34 and/or cathode 36. One or both of anode 34 and cathode 36 can also be plated with one or more materials that can aid in the disinfection process such as, for example, silver. AIRVPD device 14 may optionally include a plurality of ultraviolet (UV) light-emitting diodes (LEDs) 43 as an additional aid to the disinfection process. UV LEDs 43 may be integrated in a UV LED bar 43 and may receive power from power source 44. UV light is efficient in disinfection of airborne viruses, and UV LEDs 43 do not require a large amount of power.

Anode 34 and cathode 36 are coupled to a converter 38 by way of respective positive and negative rails 40, 42 associated with converter 38. Converter 38 receives power from a power source 44 and outputs a direct current (DC) power to anode and cathode 34, 36 that has a high voltage and a low current. Power source 44 may also power fan 30 and UV LEDs 43. The level of current that converter 38 outputs to anode 34 and cathode 36 is usually less than 1 mA, and the level of voltage converter 38 provides to anode 34 and cathode 36 is generally between approximately 2,500 V and approximately 5,000 V, depending on the distance between the anode and cathode. As a non-limiting example, when anode 34 and cathode 36 are spaced apart by approximately 0.1 inches (0.254 centimeters), converter 38 may supply approximately 2,500 V to anode 34 and cathode 36. As another non-limiting example, when the distance between anode 34 and cathode 36 is approximately 0.2 inches (0.508 centimeters), converter 38 may provide approximately 4,500 V to anode 34 and cathode 36.

Although converter 38 and power source 44 are shown external to housing 18 in FIG. 1, converter 38 and/or power source 44 may or may not be positioned within housing 18. As a non-limiting example, power source 44 may be a battery within a battery compartment (not shown in FIG. 1) that outputs a DC power, and converter 38 may be a DC-to-DC converter such as, for example, a high-frequency DC-to-DC step-up converter that operates at a high efficiency and does not emit an audible noise to a user of AIRVPD device 14. In that case, both DC-to-DC converter 38 and battery 44 may be positioned in interior 23 of housing 18. As another non-limiting example, power source 44 may be an alternating current (AC) power source or DC power source external to AIRVPD device 14, such as, for example, a DC battery, a generator, or the utility power from an electrical socket. When power source 44 is an AC power source, converter 38 may be an AC-to-DC converter positioned either external to or in interior 23 of housing 18.

Since converter 38 provides a high voltage to anode 34 and cathode 36, AIRVPD device 14 is typically equipped with safety electronics. More specifically, in some embodiments, AIRVPD device 14 will include optional humidity sensors 48 to detect when a level of humidity is too high or if AIRVPD device 14 is submerged in liquids accidentally, especially in the case that AIRVPD device 14 is a personal and portable apparatus. Humidity sensors 48 are positioned in various locations in AIRVPD device 14 so that liquids can be immediately detected in the event AIRVPD device 14 is submerged. Additionally, AIRVPD device 14 may include a spark detector 50. Sparks could appear between anode 34 and cathode 36 due to various environmental conditions. If humidity sensors 48 sense that the humidity in AIRVPD device 14 has reached or crossed a preset humidity threshold or spark detector 50 detects a spark between anode 34 and cathode 36, converter 38 will stop providing power to anode 34 and cathode 36 and an alarm will be triggered.

According to the configuration of AIRVPD device 14 described above, AIRVPD device 14 is able to protect against and disinfect droplets bodily fluid that are infected with airborne viruses. Initially, ionized air with charged droplets 16 is drawn into AIRVPD device 14 through opening 24 of inlet 20 of housing 18 by fan 30 before coming into contact with an individual or individuals in the area. Ionized air with charged droplets 16 passes through HEPA filter 28 and fan 30 before reaching anode 34 and cathode 36. At this point, converter 38 is delivering the high-voltage, low-current DC power to anode 34 and cathode 36 to trigger or induce a redox reaction at anode 34 and cathode 36. That is, the application of the high-voltage, low-current DC power to anode 34 and cathode 36 results in oxidation occurring at anode 34 and reduction occurring at cathode 36. The redox reaction thus causes a decrease in electrons at anode 34 and an increase of electrons at cathode 36. As such, anode 34 is positively charged to attract negatively charged particles and cathode is negatively charged to attract positively charged particles. Thus, positively charged air ions and droplets in ionized air with charged droplets 16 will be attracted to cathode 36, and negatively charged air ions and droplets in ionized air with charged droplets 16 will be attracted to anode 34.

Once ionized air with charged droplets 16 reaches anode 34 and cathode 36, it flows through electrode fluid path 35, where the charged droplets of bodily fluid are deposited on anode 34 and/or cathode 36. The associated air ions and charged droplets of bodily fluid are neutralized by anode 34 and cathode 36 and disinfected by the antimicrobial of chemical disinfecting unit 46. The antimicrobial disinfects any infected droplets of bodily fluid almost instantly upon contact. As ionized air with charged droplets 16 is being neutralized and initially disinfected, UV LEDs or UV LED bar 43 provides additional disinfection. After the neutralization and disinfection process is complete, the neutralized and disinfected droplets of bodily fluid evaporate from anode 34 and/or cathode 36 and pass through opening 26 of outlet 22 of housing 18 with the neutralized air particles as clean air 51. By collecting the droplets of bodily fluid on anode 34 and/or cathode 36 and allowing them to evaporate, AIRVPD device 14 will kill the germs in the droplets without affecting the humidity of the air around AIRVPD device 14.

Referring now to FIGS. 2-12, a plurality of configurations of AIRVPD device 14 are shown, according to embodiments of the invention. The AIRVPD devices shown in FIGS. 2-12 are arranged similarly to AIRVPD device 14 and, thus, like element therein are numbered identical to corresponding elements in AIRVPD device 14. Further, in the AIRVPD devices shown in FIGS. 2-12, chemical disinfecting unit 46 is only associated with cathode 36. However, as described above, chemical disinfecting unit 46 may be associated with anode 34 as an alternative or in addition to cathode 36, depending on the charge ionizer 12 is configured to produce in ionized air with charged droplets 16, which is not shown in FIGS. 2-12 for the purpose of clarity. Further, the positioning of the various components in the AIRVPD devices of FIGS. 2-12 are non-limiting and can be varied based on preference and/or in order to optimize utility of the components. For example, UV LED bar 43 may be positioned at various locations within housing 18 including on the opposite side of anode 34 and cathode 36 from that shown.

Figure 2:
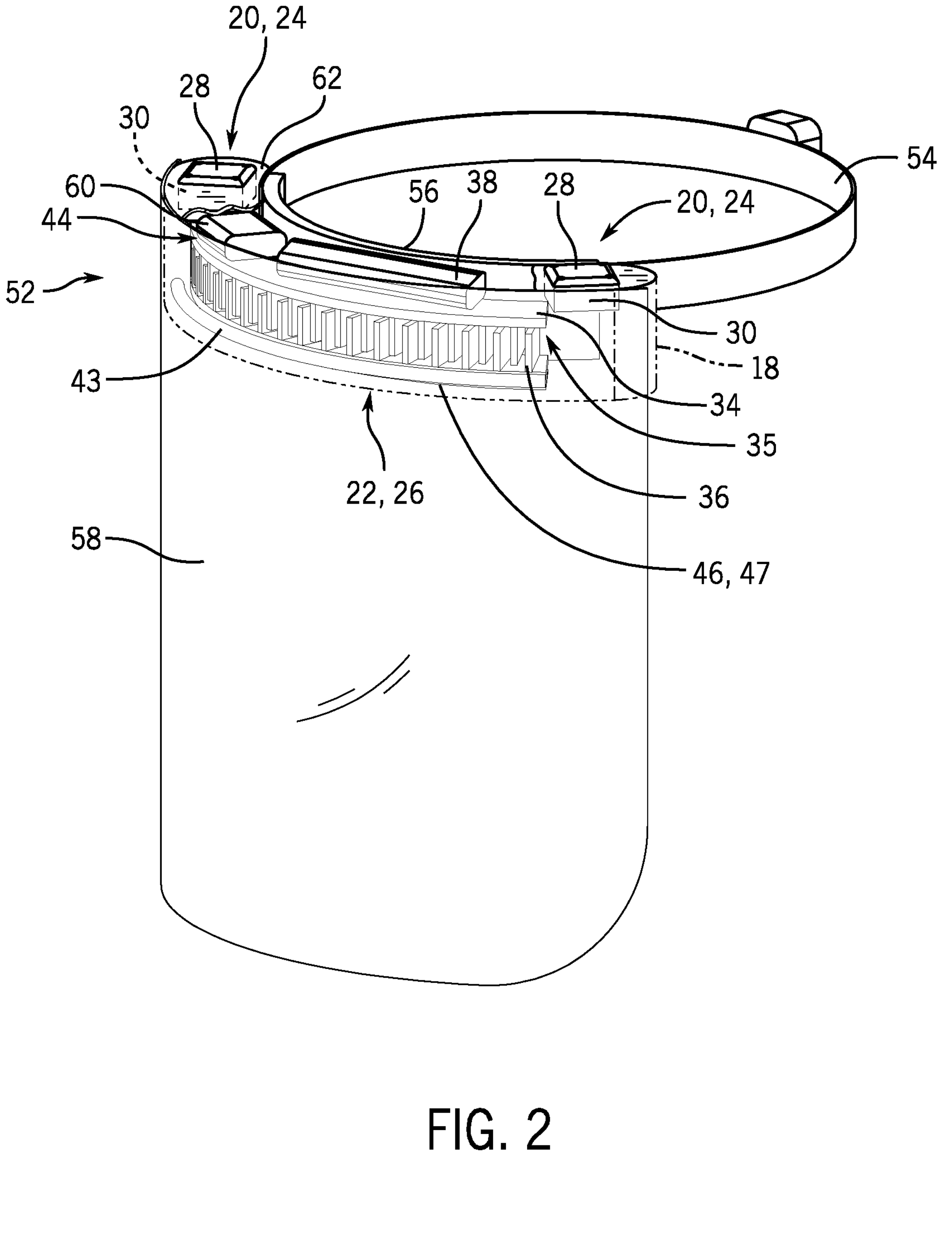
FIGS. 2 and 3 are perspective top and bottom views, respectively, of a personal and portable AIRVPD device wearable on a user's head, according to an embodiment of the invention.
Figure 3:
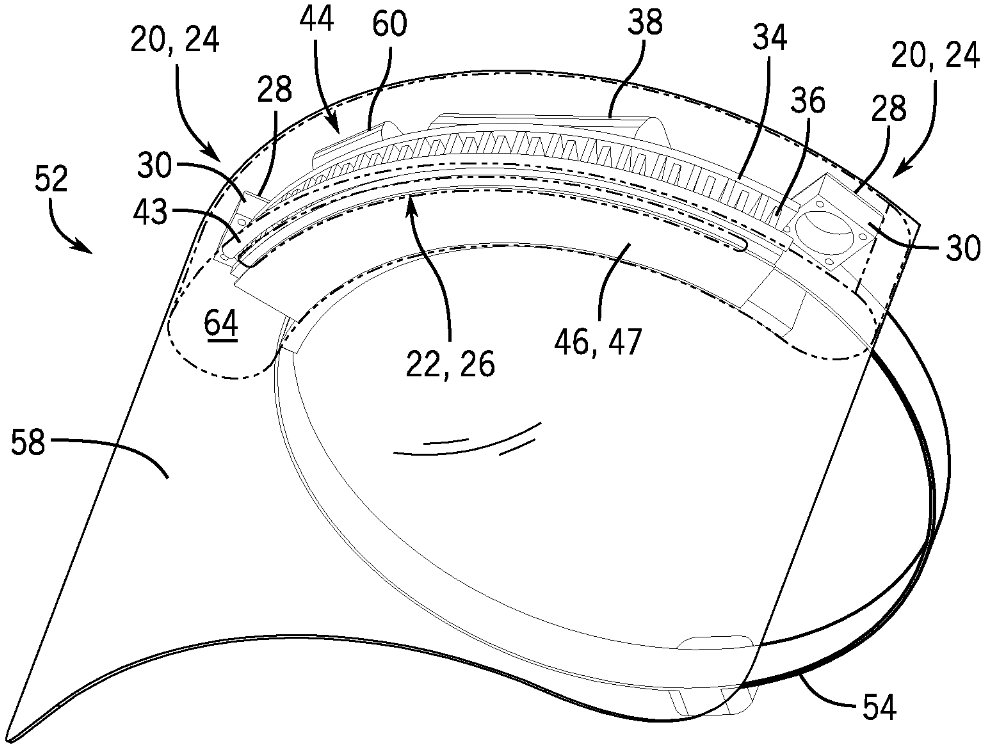

Referring initially to FIGS. 2 and 3, perspective top and bottom views of an AIRVPD device 52 are shown, according to an embodiment of the invention. AIRVPD device 52 is designed as a personal and portable device wearable on a user's head. That is, AIRVPD device 52 includes an adjustable bracket 54 such that an individual can wear AIRVPD device 52 like a hat or visor. Adjustable bracket 54 includes a head rest 56, such as, for example, a sponge or other comfortable and/or absorbent material, for a user's forehead in order to make wearing AIRVPD device 52 more comfortable and/or to absorb perspiration. AIRVPD device 52 further includes a face shield 58 for additional user protection from infected droplets of bodily fluid.

Since AIRVPD 52 is configured for personal use, power source 44 in AIRVPD device includes one or more DC batteries located in a battery compartment 60, and converter 38 is a DC-to-DC converter. As a non-limiting example of power source 44, power source 44 could include two 9-V batteries in a battery compartment 60 that can be replaced by a user of AIRVPD device 52, as necessary. DC batteries 44 provide power to DC-to-DC converter 38 and to two fans 30 with corresponding HEPA filters 28. Fans 30 draw ionized air with charged droplets into two openings 24 of inlet 20 in a top surface 62 of housing 18 and through HEPA filters 28 to anode 34 and cathode 36. Generally, anode 34 and cathode 36 are spaced apart by approximately 0.1 inches (0.254 centimeters) in this embodiment so that converter 38 can supply a voltage at the low end of the voltage range—approximately 2,500 V. After passing through electrode fluid path 35 between anode 34 and cathode 36 and chemical disinfection unit 46 in the form of a strip of sponge material 47, the ionized air with charged droplets 16 has been neutralized and disinfected. Additional disinfection is provided by UV LED bar 43 before the now clean air passes through opening 26 of outlet 22, which is a slit in a bottom surface 64 of housing 18.

Figure 4:
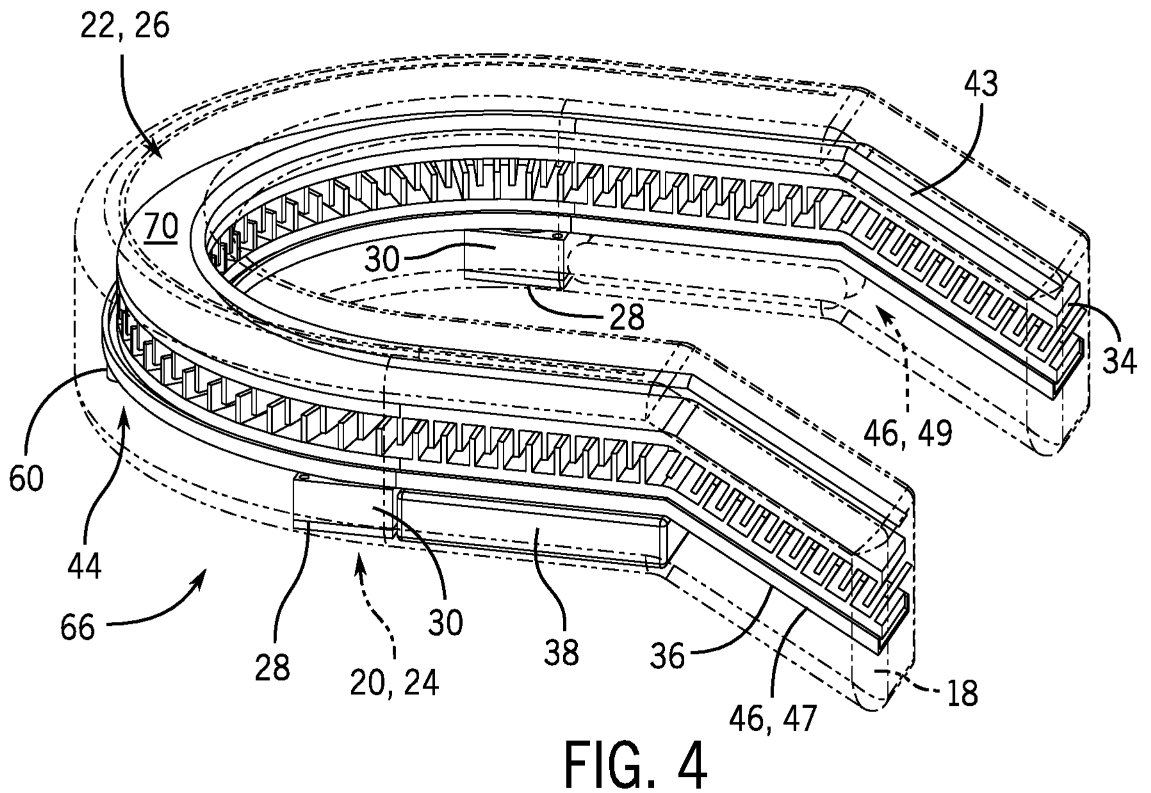
FIGS. 4 and 5 are perspective top and bottom views, respectively, of a personal and portable AIRVPD device wearable around a user's neck, according to an embodiment of the invention.
Figure 5:
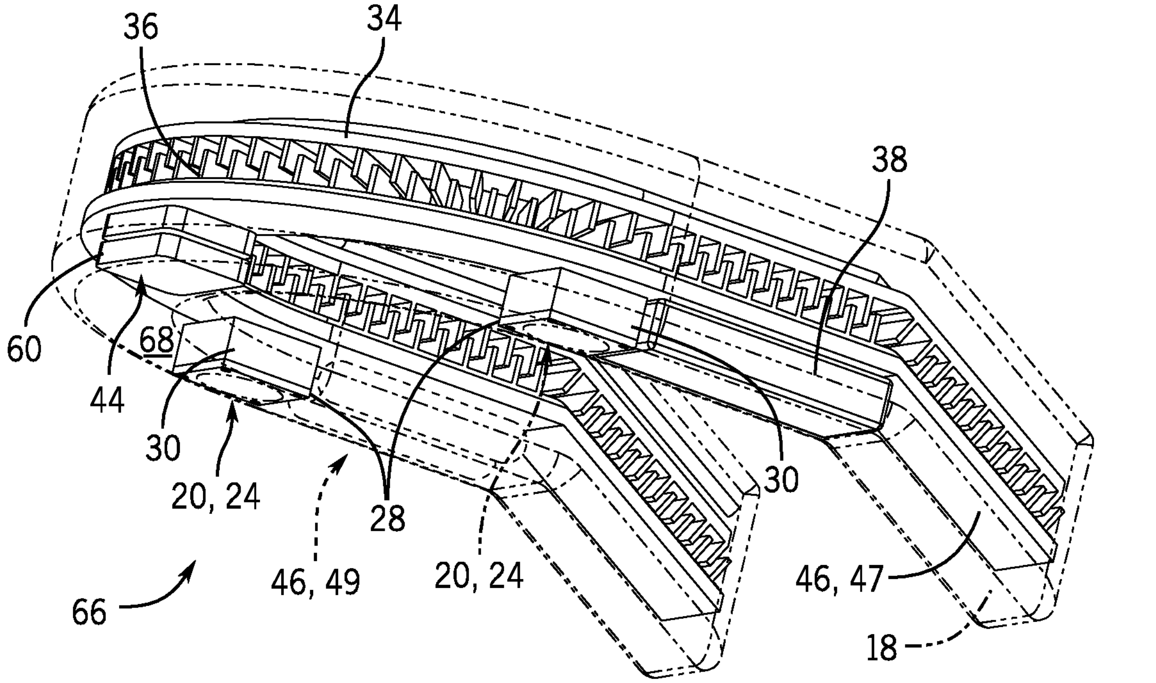

Referring now to FIGS. 4-5, perspective top and bottom views of an AIRVPD device 66 are shown, according an embodiment of the invention. AIRVPD device 66 is designed as a personal and portable device wearable around a user's neck. That is, housing 18 is arranged as a collar in s U-shape to fit around a user's neck on top of the shoulders. Similarly to AIRVPD device 52 shown in FIGS. 2-3, since AIRVPD device 52 is a personal device, power source 44 includes one or more DC batteries, such as, for example, two 9-V batteries, in battery compartment 60, and converter 38 is a DC-to-DC converter. DC batteries 44 provide power to DC-to-DC converter 38 and to two fans 30 with corresponding HEPA filters 28.

Fans 30 draw ionized air with charged droplets into two openings 24 of inlet 20 in a bottom surface 68 of housing 18 and through HEPA filters 28. After passing through HEPA filters 28, the ionized air with charged droplets 16 travels to anode 34 and cathode 36, which are preferably, but not necessarily spaced apart by approximately 0.1 inches (0.254 centimeters). When the distance between anode 34 and cathode 36 is approximately 0.1 inches (0.254 centimeters), DC-to-DC converter 38 may apply a voltage of approximately 2,500 V to the anode 34 and cathode 36. When the ionized air with charged droplets passes through electrode fluid path 35 between anode 34 and cathode 36 and chemical disinfection unit 46 in the form of a strip of sponge material 47 and optional reservoirs 49, the ionized air with charged droplets 16 has been neutralized and once-disinfected. UV LED bar 43 is arranged in housing 18 after chemical disinfection unit 36 in order to provide a second round of disinfection. After being neutralized and twice-disinfected, the now clean air flows through opening 26 of outlet 22, which is arranged as a slit in a top surface 70 of housing 18.

Figure 6:
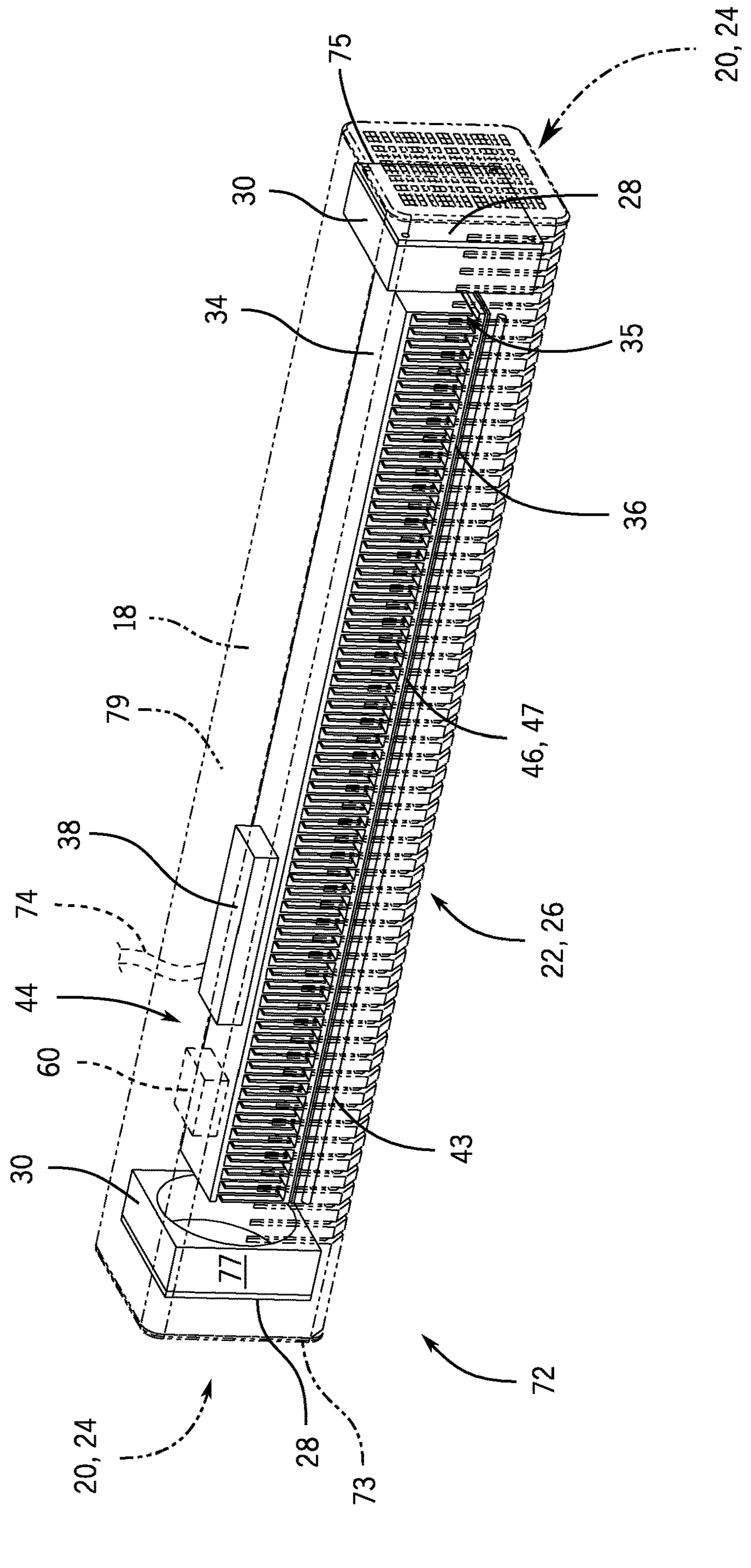
FIG. 6 is a top perspective view of an AIRVPD device for use on a surface or with an apparatus, according to an embodiment of the invention.

Referring now to FIG. 6, a top perspective view of an AIRVPD device 72 is shown, according to an embodiment of the invention. One or more AIRVPD devices 72 can be configured for a variety of different applications. Housing 18 of AIRVPD device 72 is substantially rectangular or bar-shaped. As AIRVPD device 72 is shown in FIG. 6, power source 44 may be in the form of DC batteries in battery compartment 60 or in the form of an external DC or AC power source 44, such as, for example, a larger DC battery, an AC generator, or utility power, coupled to AIRVPD device 72 via wiring 74, which may be direct wiring or a power cable such as, for example, an AC power cable for an electrical socket. In the case that AC power is delivered via wiring 74, converter 38 may be in the form of an AC-to-DC converter.

Power source 44 delivers power to converter 38 and two fans 30, each having a corresponding HEPA filter 28. In operation, fans 30 draw ionized air with charged droplets through a plurality of openings 24 in inlet 20 located at each of two ends 73, 75 of housing 18 and HEPA filter 28 to the electrode path 35 between anode 34 and cathode 36, which are spaced apart by approximately 0.1 inches (0.254 centimeters). Converter 38 thus supplies approximately 3,500 V to anode 34 and cathode 36. The ionized air with charged droplets passing through electrode fluid path 35 is neutralized and disinfected with the antimicrobial impregnated in sponge material 47 of chemical disinfecting unit 46. Thereafter, the neutralized and once-disinfected air with droplets passes by UV LED bar 43 for supplemental disinfection before exiting housing 18 through a plurality of openings 26 in outlet 22 located on a side 77 of housing 18 as clean air.

As noted above, AIRVPD device 72 may be configured for use on a surface such as, for example, a desktop, countertop, or even the floor. This surface configuration is meant for personal use in an area around a user in an office or similar or type of room. As a non-limiting example of use for AIRVPD 72 in this context, a single AIRVPD device 72 may be used for one person in a room with an approximately 1,400 cubic foot (approximately 40 cubic meter) volume. The design allows users to easily carry surface AIRVPD device 72 from room to room without having to wear surface AIRVPD device 72. However, surface AIRVPD device 72 works best when left in the same area for an extended period of time such as, for example, 30 minutes. Surface AIRVPD device 72 typically includes power source 44 in the form of DC batteries in battery compartment 60, but may alternatively couple to an external power source 44 via wiring 74.

Figure 7:
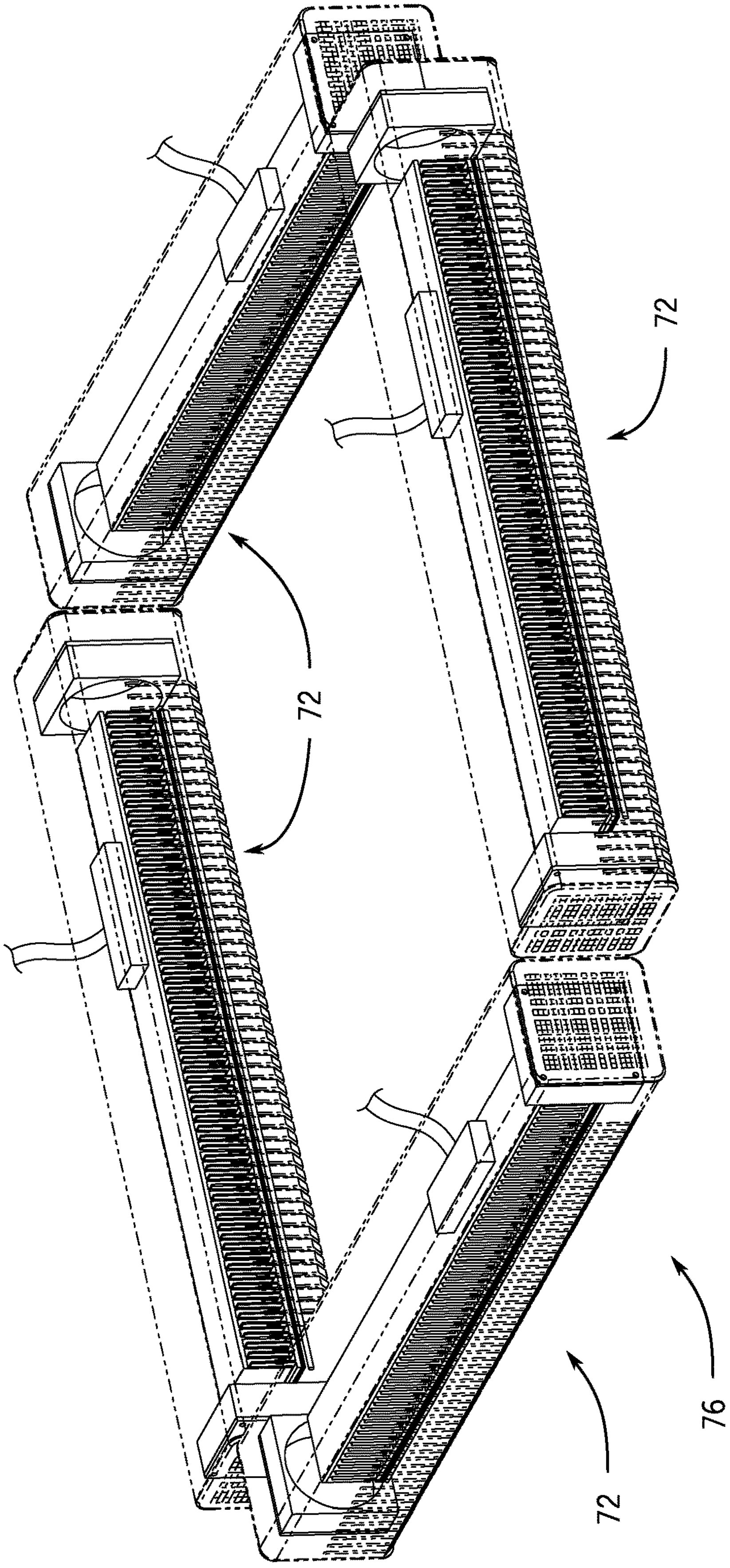
FIG. 7 is a perspective view of a modular arrangement of a plurality of the AIRVPD device shown in FIG. 4 for protecting a user sitting in or standing at an apparatus, according to an embodiment of the invention.

Referring now to FIG. 7, a perspective view of a modular arrangement 76 of a plurality of AIRVPD devices 72 for protecting a user sitting in or standing at an apparatus is shown, according an embodiment of the invention. Arrangement 76 may be used with a variety of different apparatus, such as, for example, a chair, a desk, a kiosk, or another similar apparatus in which a user may sit or at which a use may stand. In the embodiment shown in FIG. 7, four AIRVPD devices 72 are illustrated. However, a different number of AIRVPD devices 72 may also be used. In order to provide protection for a user sitting in or standing at the apparatus, arrangement 76 of AIRVPD devices 72 is positioned at some point above the apparatus by either mounting them to the apparatus or to the ceiling above the apparatus.

In this embodiment, each AIRVPD device 72 is designed in the same manner as for use on a surface, with the exception that, in arrangement 76, AIRVPD device 72 typically includes wiring 74 to an external AC or DC power source 44 rather than an internal DC power source 44. As such, converter 38 may be an AC-to-DC converter. In various embodiments, external power source 44 is an independent power source included in the apparatus. As a non-limiting example, the apparatus may include a DC battery, in which case converter 38 would be a DC-to-DC converter. In any case, arrangement 76 of AIRVPD devices 72 results in a jet of air forming around the apparatus and drawing in all ionized air with charged droplets such that an infected droplet of bodily fluid has essentially no chance to reach a user sitting in or standing at the apparatus.

Figure 8:
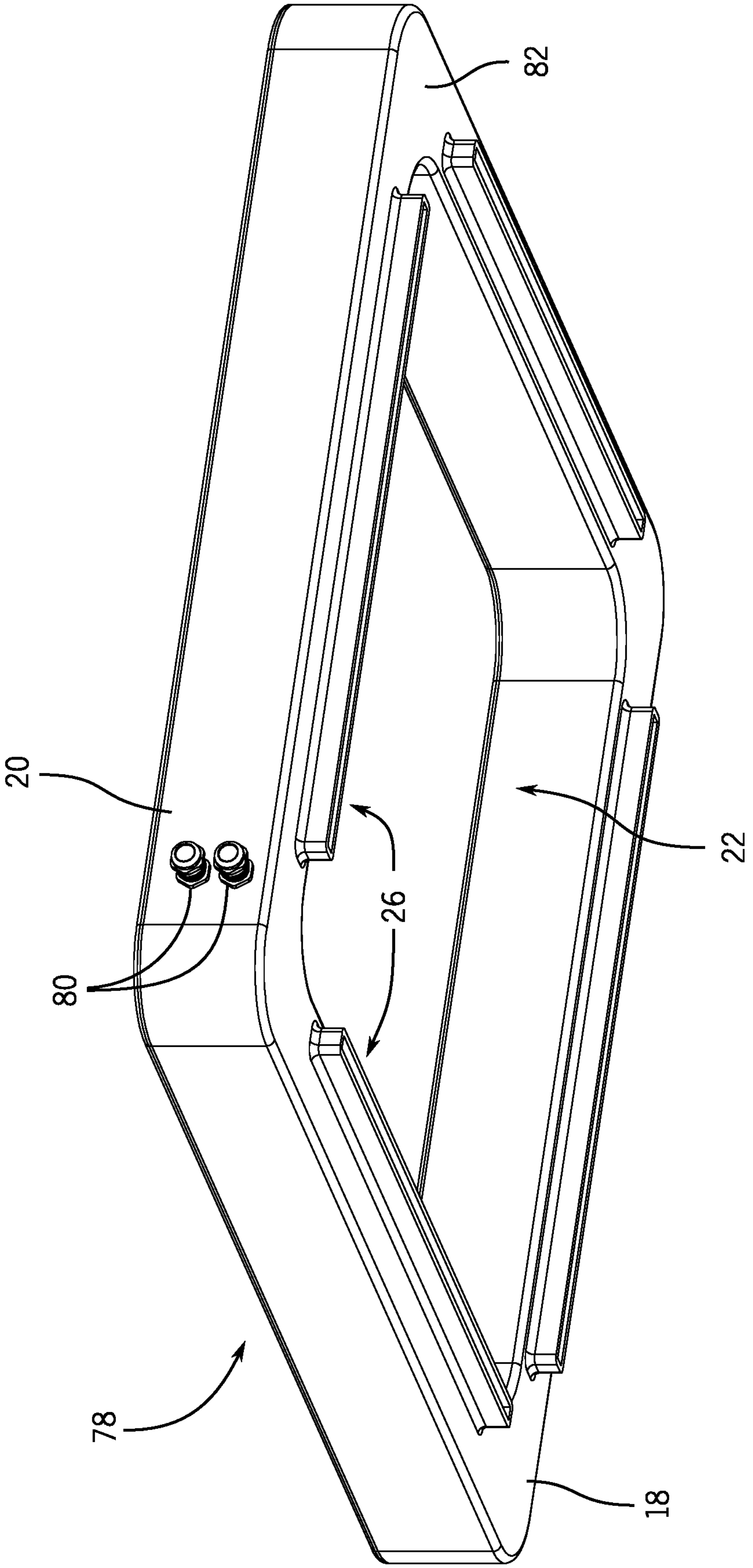
FIGS. 8 and 9 are bottom and top perspective views, respectively, of an integrated AIRVPD device for protecting a user sitting in or standing at an apparatus, according to an embodiment of the invention.
Figure 9:
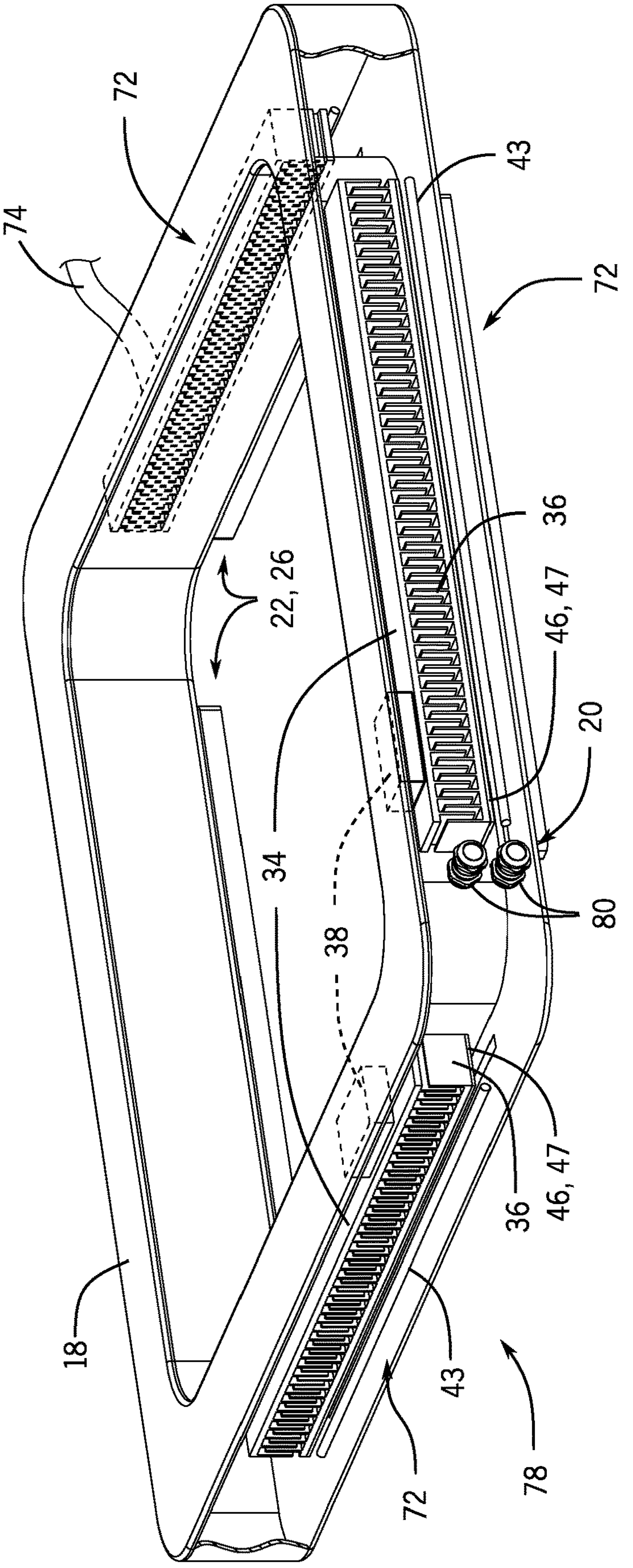

Referring now to FIGS. 8 and 9, bottom and top perspective views, respectively, of an integrated AIRVPD device 78 for use with an apparatus is shown, according to an embodiment of the invention. Integrated AIRVPD device 78 is a modified version of arrangement 76 of AIRVPD devices 72 of FIG. 7, with the components of each AIRVPD device 72 being integrated into a single housing 18. More specifically, integrated AIRVPD 78 includes a plurality of anodes 34, cathodes 36, converters 38, UV LED bars 43, and chemical disinfecting units 46 that form a plurality of AIRVPD devices 72 in integrated housing 18. Thus, integrated AIRVPD device 78 may be used in a similar manner as arrangement 76 of AIRVPD devices 72. As such, integrated AIRVPD device 78 is essentially a merging of the four AIRVPD devices 72 illustrated in FIG. 7 into a single housing 18. Thus, similarly to arrangement 76 of AIRVPD devices 72, integrated AIRVPD device 78 is positioned above an apparatus by mounting it to the apparatus or to the ceiling above the apparatus and includes wiring 74 coupled to an external power source 44 such as a generator, an electrical socket, or a DC battery within the apparatus, as non-limiting examples.

However, in integrated AIRVPD device 78, each anode 34 and cathode 36 pair is spaced apart by approximately 0.2 inches (0.508 centimeters), and converter 38 supplies approximately 4,500 V to anode 34 and cathode 36. Further, integrated AIRVPD device 78 does not include any internal fans. Instead, an external supply of ionized air is supplied by ionizer 12 (shown in FIG. 1), which is coupled to inlet 20 at inlet ports 80. Alternatively, ionizer 12 may supply ionized air as a built-in ionizer. Further, outlet 22 of integrated AIRVPD device 78 includes a plurality of openings 26 on a bottom surface 82 of housing 18. Like arrangement 76 of AIRVPD devices 72, operation of integrated AIRVPD 78 results in results in a jet of air forming around the apparatus associated therewith. The jet of air draws in charged droplets of bodily fluid such that an infected droplet of bodily fluid has essentially no chance of reaching the apparatus.

Figure 10:
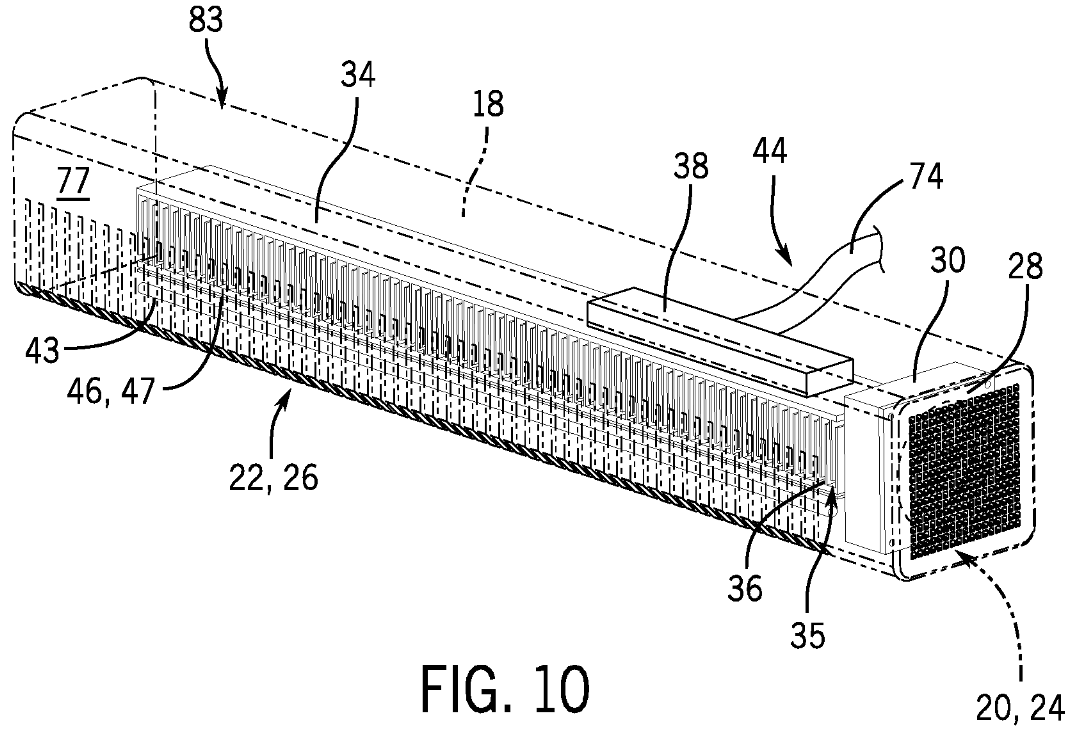
FIGS. 10 and 11 are perspective top views of an AIRVPD device for protecting an entire room, according to an embodiment of the invention.
Figure 11:
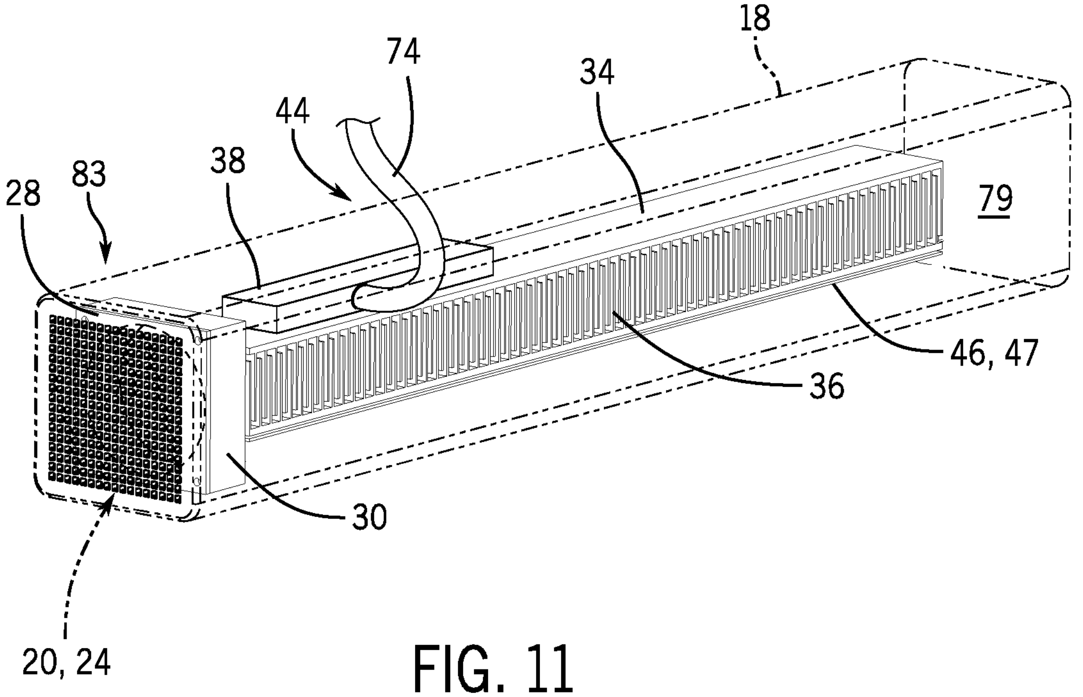

Referring now to FIGS. 10 and 11, perspective top views of an AIRVPD device 83 for protecting an entire room is shown, according to an embodiment of the invention. AIRVPD device 83 shares many characteristics of AIRVPD device 72 shown in FIG. 6. However, AIRVPD device 83 differs from AIRVPD device 72 shown in FIG. 6 in that it includes one fan 30 and HEPA filter 28 at end 75 of housing 18 and one set of openings 26 of outlet 22 on side 77 of housing 18. Further, AIRVPD device 83 is coupled to an external power source 44 via wiring 74, and external power source 44 supplies 4,500 V to anode 34 and cathode 36, which are spaced apart by approximately 0.2 inches (0.508 centimeters). Depending on the location of AIRVPD device 83, it may be beneficial to wire AIRVPD device 83 directly into an electrical circuit with wiring 74 rather than including wiring 74 as a power cable for plugging into an electrical socket. While the principle of operation of AIRVPD device 83 is essentially the same as that of AIRVPD 72 shown in FIG. 6, the different configuration of AIRVPD device 83 allows AIRVPD device 83 to protect an entire room (not shown in FIG. 10 or 11).

Typically, AIRVPD device 83 will be mounted on the ceiling or high on the wall in a room. Hence, AIRVPD device 83 will be positioned farther away from a user and can incorporate a larger, more powerful fan 30 therein. This larger, more power fan 30 enables AIRVPD device 83 to protect a greater area that AIRVPD device 72 of FIG. 6 such as an entire room. While such a fan 30 may be noisier, it will have minimal or no effect on the user due to the larger distance away from the user. Further, having openings 26 of outlet 22 only on side 77 of housing 18 provides for AIRVPD device 83 to be positioned on the perimeter of a room on a wall or ceiling. In any case, side 77 of housing 18 with openings 26 of outlet 22 will ideally be positioned such that outlet 22 is directed toward the middle or center of a room in order to provide clean air into the environment.

Figure 12:
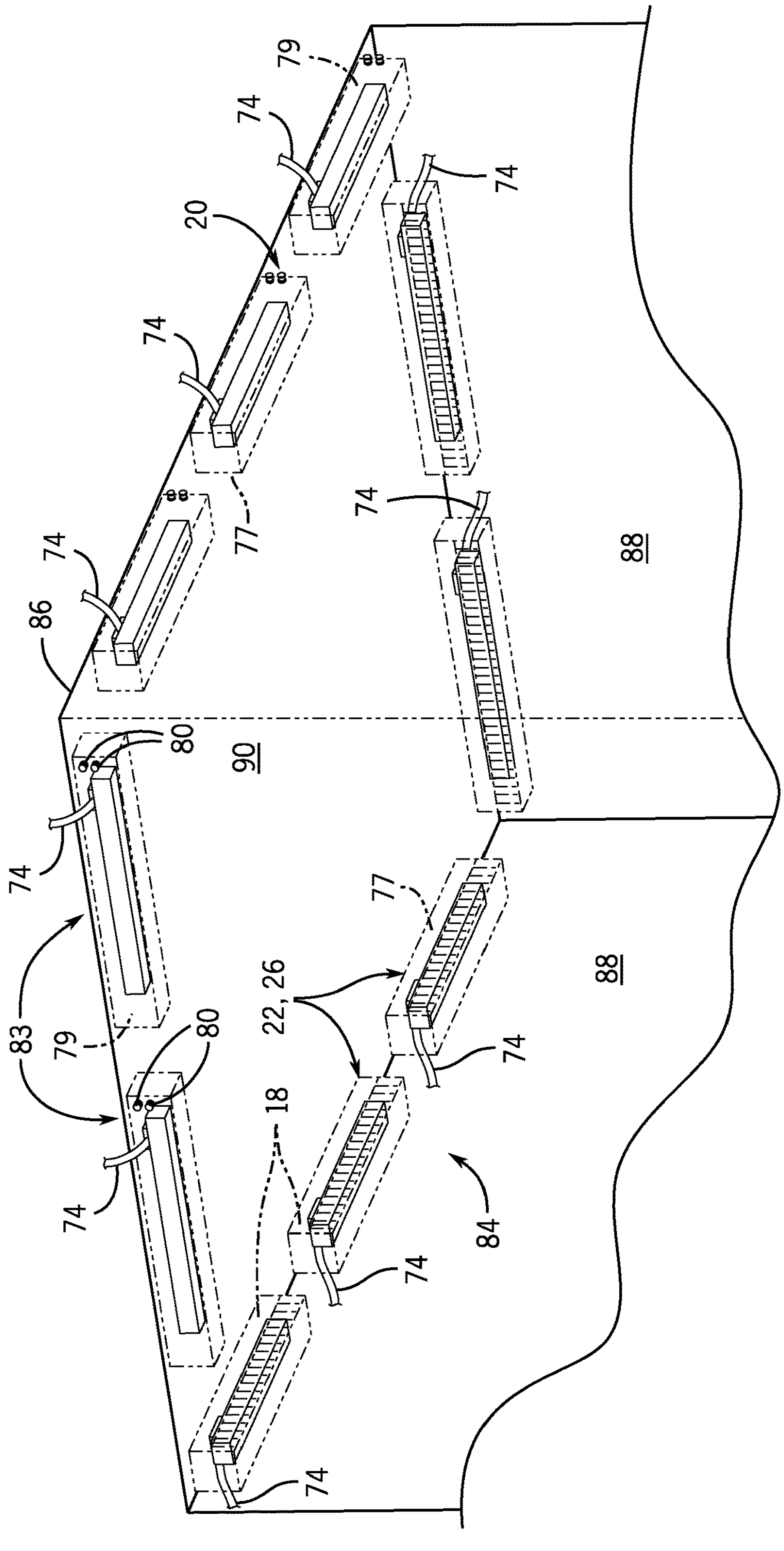
FIG. 12 is a perspective view of a plurality of the module AIRVPD device shown in FIGS. 10-11 arranged for protecting a large area, according to an embodiment of the invention.

Referring now to FIG. 12, a perspective view of an arrangement 84 of a plurality of AIRVPD devices 83 for a large area 86 is shown, according to an embodiment of the invention. In FIG. 12, large area 86 is a room 86 with four walls 88 and a ceiling 90, but large area 86 is not limited to such a configuration. Although 10 AIRVPD devices 83 are illustrated in FIG. 12, a different number of AIRVPD devices 83 may be used, depending on the size of large area 86 and the spacing between AIRVPD devices 83. As a non-limiting example, AIRVPD devices 83 may be spaced apart by approximately 24 inches (60.96 centimeters) or more, but this may vary based on the configuration of room 86.

In arrangement 84 of FIG. 12, AIRVPD devices 83 are designed in the same manner as that shown in FIGS. 10 and 11, except that, inlet 20 includes inlet ports 80, as similarly described above with respect to FIGS. 8 and 9. As such, AIRVPD devices 83 do not include fan 30 or HEPA filter 28, but instead receives an external supply of ionized air through inlet ports 80. Inlet ports 80 are located on side 79 of housing 18 facing adjacent walls 90 of room 86 and opposite side 77 of housing including openings 26 of outlet 22. As similarly explained above with respect to FIGS. 10 and 11, side 77 of housing 18 of each AIRVPD device 83 should be positioned facing the center of room 86. In this manner, outlet 22 is able to direct clean air into the environment.

Beneficially, embodiments of the invention thus provide an AIRVPD device having a pair of electrodes including an anode and a cathode receiving a high-voltage, low-current power from a converter coupled to a power supply. The AIRVPD device further includes a chemical disinfecting unit associated with at least one of the anode and cathode and including a supply of an antimicrobial for killing airborne viruses. Optionally, the AIRVPD device includes a plurality of UV LEDs or UV LED bar for additional disinfecting. The pair of electrodes, converter, chemical disinfecting unit, and UV LED bar are encased by a housing having an inlet and an outlet. A fan or other air supply positioned either in the interior of housing or externally connected to the inlet of the housing will direct ionized air with charged droplets ionized/charged by an ionizer associated with the AIRVPD device into the housing. The ionized air with charged droplets will pass through an electrode fluid path between the anode and cathode, where the charge of the ionized air with charged droplets is neutralized and any infected droplets of bodily fluid is disinfected by the antimicrobial of the chemical disinfecting unit. Thereafter, the neutralized and once-disinfected air with droplets is additionally disinfected by the UV LED bar before passing through the outlet of the housing as clean air. The many different configurations of the AIRVPD device enable it to be portable or stationary and enable it to protect individuals from contracting airborne viruses on a personal level, in a room, or in larger areas. The AIRVPD device prevents contact with airborne viruses and provides disinfection of airborne viruses simultaneously and with a high efficiency.

Therefore, according to one embodiment of the invention, an AIRVPD device includes a positive electrode and a negative electrode in close proximity to, but spaced away from, the positive electrode to form an electrode fluid path between the positive and negative electrodes. The AIRVPD device additionally includes a high-voltage converter configured to deliver power to the positive and negative electrodes in order to trigger a redox reaction at each of the positive and negative electrodes such that the positive electrode attracts negatively charged particles and the negative electrode attracts positively charged particles. Furthermore, the AIRVPD device includes a chemical disinfecting unit having a sponge material associated with and extending along a length of at least one of the positive and negative electrodes. The sponge material is capable of becoming impregnated with an antimicrobial capable of killing airborne viruses. Moreover, the AIRVPD device includes a housing encasing the positive and negative electrodes, the high-voltage converter, and the chemical disinfecting unit and including an inlet and an outlet in fluid communication with each other via the electrode fluid path. The housing is configured such that ionized air with charged droplets external to the AIRVPD device is able to flow into the AIRVPD device through the inlet of the housing, through the electrode fluid path for disinfection by the antimicrobial and for neutralization by the positive and negative electrodes, and through the outlet of the housing and out of the AIRVPD device.

According to another embodiment of the present invention, a kit for protection against and disinfection of airborne viruses includes an ionizer configured to produce ions for electrically charging air having droplets and at least one AIRVPD device. The at least one AIRVPD device includes a converter configured to convert a power from a power supply to a high-voltage, low-current power across a positive side and a negative side thereof and a pair of electrodes having a cathode coupled to the negative side of the converter and an anode coupled to the positive side of the converter and positioned adjacent to, but electrically isolated from, the cathode. The cathode and anode are configured to receive the high-voltage, low-current power from the converter to induce a redox reaction at the cathode and anode and are arranged to form an electrode fluid path therebetween. The at least one AIRVPD device also includes a chemical disinfecting unit with a sponge material arranged on at least one of the cathode and anode and capable of impregnation with an antimicrobial capable of killing airborne viruses. The sponge material is configured to supply the antimicrobial to the at least one of the cathode and anode.

In addition, the at least one AIRVPD device includes a case positioned around the converter, the pair of electrodes, and the chemical disinfecting unit. The case includes an inlet and an outlet in fluid communication with each other through the electrode fluid path. Ionized air having charged droplets is able to flow into the AIRVPD device through the inlet of the case, along the electrode fluid path for charge neutralization and disinfection, and through the outlet of the case to exit the AIRVPD device.

According to yet another embodiment of the present invention, a method of manufacturing an AIRVPD device includes arranging a pair of electrodes comprising a positive electrode and a negative electrode in close proximity to, but electrically isolated from, one another to form an electrode fluid path therebetween. The method further includes coupling a high-voltage converter to the positive and negative electrodes for introducing a redox reaction at the positive and negative electrodes and positioning a chemical disinfecting unit including a sponge material capable of becoming impregnated with an antimicrobial adjacent to at least one of the positive and negative electrodes to deliver the antimicrobial to the at least one of the positive and negative electrodes adjacent thereto. The method additionally includes encasing the positive and negative electrodes, the high-voltage converter, and the chemical disinfecting unit in a housing comprising an inlet and an outlet in fluid communication with each other and the electrode fluid path.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. An airborne virus protection and disinfection (AIRVPD) device comprising (a) a housing comprising a first opening and a second opening distal from the first opening, wherein the housing forms an enclosed passageway between the first opening and the second opening capable of channeling a flow of air from the first opening to the second opening;

(b) a pair of electrodes located within the enclosed passageway, wherein the pair of electrodes comprises a first electrode and a second electrode, wherein the second electrode is spaced apart from, and proximal to, the first electrode, wherein the pair of electrodes forms an electrode fluid path between the pair of electrodes capable of channeling a flow of air between the pair of electrodes received from the first opening toward the second opening; and (c) a sponge-like material located within the enclosed passageway between the first opening and the second opening, wherein the sponge-like material is capable of becoming impregnated with an antimicrobial substance, wherein the sponge-like material is arranged within the enclosed passageway such that at least a portion of the enclosed passageway forms a channel comprising the sponge-like material, wherein the portion of the enclosed passageway is capable of channeling a flow of air from the first opening to the second opening contacting the sponge-like material without passing through the sponge-like material.

2. The AIRVPD device according to claim 1, wherein the sponge-like material is arranged on, or adjacent to, at least one of the first electrode and the second electrode.

3. The AIRVPD device according to claim 2, wherein the sponge-like material extends along the length of at least one of the first electrode and the second electrode.

4. The AIRVPD device according to claim 1, wherein the AIRVPD device further comprises a high-voltage converter electrically coupled to the first electrode and the second electrode, wherein the high-voltage converter is configured to deliver power to the first and second electrodes comprising a voltage such that the first electrode is provided with a positive charge and the second electrode is provided with negative charge.

5. The AIRVPD device according to claim 4, wherein the AIRVPD device further comprises a battery capable of being coupled with the high-voltage converter for supplying power to the high-voltage converter.

6. The AIRVPD device according to claim 4, wherein the AIRVPD device further comprises wiring coupled with the high-voltage converter, wherein the wiring is couplable to an external power supply.

7. The AIRVPD device according to claim 4, wherein the high-voltage converter is configured to supply a voltage in the range from between approximately 2,500 V and approximately 5,000 V.

8. The AIRVPD device according to claim 1, wherein each of the first electrode and the second electrode comprises a base;

a plurality of fins extending outward from the base; and a plurality of cavities between adjacent fins of the plurality of fins, wherein the fins of the first electrode extend into the cavities of the second electrode and the fins of the second electrode extend into the cavities of the first electrode.

9. The AIRVPD device according to claim 1, wherein the first and second electrodes are spaced apart by a distance in a range between approximately 0.1 inches (0.254 centimeters) and approximately 0.2 inches (0.508 centimeters).

10. The AIRVPD device according to claim 1, wherein the sponge-like material is sponge copper.

11. The AIRVPD device according to claim 1 further comprising an ultraviolet light emitting diode bar positioned within the housing to disinfect air.

12. The AIRVPD device according to claim 1 further comprising a fan disposed in the housing between the first opening and the second opening, wherein the fan is capable of generating a flow of air from the first opening to the second opening.

13. A kit for protection against and disinfection of airborne viruses comprising an ionizer configured to produce ions for electrically charging air having droplets and at least one airborne virus protection and disinfecting (AIRVPD) device according to claim 1.

14. The kit according to claim 13, wherein the pair of electrodes of the at least one AIRVPD device is arranged in a hair comb-style arrangement.

15. The kit according to claim 13, wherein the at least one AIRVPD device further comprises a fan positioned within the case and configured to direct ionized air having charged droplets into the at least one AIRVPD device through the first opening.

16. The kit according to claim 13, wherein at least one electrode of the pair of electrodes of the AIRPVD device is plated with silver.

17. A method for manufacturing an airborne virus protection and disinfection (AIRPVD) device comprising arranging a pair of electrodes in close proximity to, but electrically isolated from, one another to form an electrode fluid path therebetween;

coupling a high-voltage converter to the pair of electrodes for introducing a redox reaction at the electrodes;

positioning a chemical disinfecting unit including a sponge-like material capable of becoming impregnated with an antimicrobial adjacent to at least one of the electrodes to deliver the antimicrobial to the at least one of the electrodes adjacent thereto; and encasing the pair of electrodes and the chemical disinfecting unit in a housing comprising a first opening and a second opening in fluid communication with each other and the electrode fluid path, wherein:

the housing forms an enclosed passageway between the first opening and the second opening capable of channeling a flow of air from the first opening to the second opening; and the sponge-like material is located within the enclosed passageway between the first opening and the second opening, wherein the sponge-like material is capable of becoming impregnated with an antimicrobial substance, wherein the sponge-like material is arranged within the enclosed passageway such that at least a portion of the enclosed passageway forms a channel comprising the sponge-like material, wherein the portion of the enclosed passageway is capable of channeling a flow of air from the first opening to the second opening contacting the sponge-like material without passing through the sponge-like material.

18. The method according to claim 17, wherein the arranging the pair of electrodes comprises (1) providing first and second electrodes, wherein the first and second electrodes each have a base, a plurality of fins extending from the base and a plurality of cavities between adjacent fins of the plurality of fins and (2) positioning the first and second electrodes in a hair comb style arrangement with fins of the first electrode inserted into cavities of the second electrode and fins of the second electrode being inserted into cavities of the first electrode.

19. The method according to claim 17 further comprising arranging an ultraviolet light-emitting diode bar within the housing between the pair of electrodes and the second opening.

20. The method according to claim 17 further comprising coupling a battery compartment to the high-voltage converter configured to receive a battery therein as the power source for the AIRVPD device.

* * * * *